United States Patent
Nebosis et al.

(10) Patent No.: US 9,633,424 B2
(45) Date of Patent: Apr. 25, 2017

(54) METHOD AND SYSTEM FOR OPTICAL COHERENCE TOMOGRAPHY

(71) Applicant: Agfa HealthCare NV, Mortsel (BE)

(72) Inventors: Rainer Nebosis, Munich (DE); Wolfgang Schorre, Wolfratshausen (DE)

(73) Assignee: Agfa HealthCare NV, Mortsel (BE)

( * ) Notice: Subject to any disclaimer, the term of this patent is extended or adjusted under 35 U.S.C. 154(b) by 143 days.

(21) Appl. No.: 14/428,653

(22) PCT Filed: Sep. 26, 2013

(86) PCT No.: PCT/EP2013/002901
§ 371 (c)(1),
(2) Date: Mar. 17, 2015

(87) PCT Pub. No.: WO2014/048573
PCT Pub. Date: Apr. 3, 2014

(65) Prior Publication Data
US 2015/0248749 A1    Sep. 3, 2015

(30) Foreign Application Priority Data
Sep. 26, 2012    (EP) .................................. 12006715

(51) Int. Cl.
*G06K 9/00*    (2006.01)
*G06T 7/00*    (2017.01)
*A61B 5/00*    (2006.01)

(52) U.S. Cl.
CPC .............. *G06T 7/00* (2013.01); *A61B 5/0059* (2013.01); *G06T 2207/10004* (2013.01); *G06T 2207/10101* (2013.01); *G06T 2207/30024* (2013.01)

(58) Field of Classification Search
CPC .............. G06T 7/00; G06T 2207/30024; G06T 2207/10004; G06T 2207/10101; G01B 9/02091; G01B 9/02; G01B 9/02012
See application file for complete search history.

(56) References Cited

U.S. PATENT DOCUMENTS 6,993,167 B1    1/2006   Skladnev et al.
7,113,288 B2*   9/2006   Fercher .............. G01B 11/2441
                                              356/479

(Continued)

FOREIGN PATENT DOCUMENTS

| | | |
|---|---|---|
| CN | 102438507 A | 5/2012 |
| JP | 2009-268733 A | 11/2009 |
| WO | 2008/154741 A1 | 12/2008 |

OTHER PUBLICATIONS

Official Communication issued in International Patent Application No. PCT/EP2013/002901, mailed on Dec. 20, 2013.

(Continued)

*Primary Examiner* — Amir Alavi
(74) *Attorney, Agent, or Firm* — Keating and Bennett, LLP

(57) ABSTRACT

A method and system for acquiring an image of an object using optical coherence tomography using an interferometer and a detector, wherein the object is irradiated with light emitted by the interferometer, light reflected by the object is fed back into the interferometer and detected by the detector, the image of the object is derived from the detected light, and a file containing information, in particular graphical information and/or photographic image information, relating to the object is assigned to and/or correlated with the image of the object.

18 Claims, 10 Drawing Sheets

(56) References Cited

U.S. PATENT DOCUMENTS

| | | | |
|---|---|---|---|
| 8,199,327 B2* | 6/2012 | Nebosis | A61B 5/0073 356/479 |
| 8,330,962 B2* | 12/2012 | Nebosis | G01N 21/4795 356/479 |
| 8,339,610 B2* | 12/2012 | Nebosis | A61B 5/0066 356/479 |
| 8,559,016 B2* | 10/2013 | Nebosis | G01N 21/4795 356/497 |
| 8,593,639 B2* | 11/2013 | Nebosis | A61B 5/0066 356/497 |
| 8,665,449 B2* | 3/2014 | Nebosis | G01B 9/02012 356/485 |
| 8,810,797 B2* | 8/2014 | Nebosis | G01B 9/02012 356/497 |
| 8,928,890 B2* | 1/2015 | Nebosis | A61B 5/0066 356/497 |
| 9,267,878 B2* | 2/2016 | Uchida | G01N 21/1702 |
| 2005/0018201 A1* | 1/2005 | de Boer | A61B 5/0059 356/479 |
| 2009/0103789 A1 | 4/2009 | Danner et al. | |
| 2010/0088346 A1 | 4/2010 | Urness et al. | |
| 2010/0149543 A1* | 6/2010 | Nebosis | G01N 21/4795 356/450 |
| 2010/0235782 A1 | 9/2010 | Powell et al. | |
| 2011/0169978 A1 | 7/2011 | Lasser et al. | |
| 2011/0234630 A1 | 9/2011 | Batman et al. | |
| 2014/0029014 A1* | 1/2014 | Nebosis | G01B 9/02012 356/479 |
| 2014/0104619 A1* | 4/2014 | Nebosis | A61B 5/0066 356/497 |
| 2015/0248749 A1* | 9/2015 | Nebosis | G06F 19/321 382/131 |

OTHER PUBLICATIONS

Official Communication issued in corresponding International Application PCT/EP2013/002901, mailed on Apr. 9, 2015.

* cited by examiner

METHOD AND SYSTEM FOR OPTICAL COHERENCE TOMOGRAPHY

CROSS-REFERENCE TO RELATED APPLICATIONS

This application is a 371 National Stage Application of PCT/EP2013/002901, filed Sep. 26, 2013. This application claims the benefit of European Application No. 12006715.2, filed Sep. 26, 2012, which is incorporated by reference herein in its entirety.

BACKGROUND OF THE INVENTION

1. Field of the Invention

The present invention relates to a method and system for optical coherence tomography.

2. Description of the Related Art

Optical coherence tomography (OCT) is a non-invasive method of investigating the inside of light-scattering specimens. Due to its light-scattering properties biological tissue is particularly suitable for diagnostic examination by OCT. Since for OCT relatively low light intensities are sufficient and the wavelengths of the light used mostly come within the near infrared range (750 nm to 1350 nm), unlike ionizing X-ray diagnostics it does not contaminate biological tissue with radiation. It is therefore particularly significant for medicine. The currently most important areas of application of OCT are in ophthalmology, dermatology and the diagnosis of cancer. However, there are also some non-medical applications, such as, e.g., in materials testing.

OCT is roughly comparable to ultrasound diagnostics, wherein, instead of sound, broadband light of a very short coherence length is used. The running times of the light reflected on different boundary layers within the specimen are recorded by an interferometer. With OCT typical resolutions higher by one or two orders of magnitude can be achieved than with ultrasound, but the measuring depth achievable is considerably smaller. Due to optical scattering the cross-section images obtained only reach into the tissue up to a depth of a few millimeters.

SUMMARY OF THE INVENTION

Preferred embodiments of the present invention provide a method and system for optical coherence tomography which is improved compared to methods and systems known from the state of the art.

The advantages and benefits of the present invention are achieved by the method and system described below.

With the method for optical coherence tomography (OCT) according to a preferred embodiment of the invention an OCT image of an object, in particular a biological tissue like the skin of a human or animal being, is acquired by an OCT system comprising an interferometer and a detector, wherein the object is irradiated with light emitted by the interferometer, light reflected by the object is fed back into the interferometer and detected by the detector and an OCT image of the object is derived from the detected light. Preferably, a data file containing information relating to the object is assigned to and/or correlated with the OCT image of the object.

The system for optical coherence tomography (OCT) for acquiring an OCT image of an object, in particular a biological tissue like the skin of a human or animal being, comprises an interferometer for outputting light with which the object can be irradiated, a detector for detecting light which is reflected by the object and fed back into the interferometer and a control unit for deriving an OCT image of the object from the detected light of the object and, preferably, for assigning and/or correlating a data file containing information relating to the object to or with, respectively, the OCT image of the object.

The invention is based on the approach, to assign additional information to the obtained OCT image or vice versa, wherein the assigned additional information characterizes the object or a part of the object, from which the OCT image was or is obtained. For example, the information assigned or to be assigned to an OCT image may contain graphical and/or photographic and/or text information relating to a region of or location on or within the object from which the OCT image was or is obtained, e.g., a body part or a specific location on a body part. Such an assignment or a correlation between the data file containing the additional information, on the one hand, and the OCT image, on the other hand, can be achieved, for example, by at least one of the following methods:

providing a memory address of the stored OCT image in the data file of the corresponding additional information and/or providing a memory address of the data file of the additional information in the data file of the corresponding OCT image and/or incorporating data of the data file of the additional information directly into the data file of the corresponding OCT image and/or incorporating data of the OCT image directly into the data file of the corresponding additional information.

As a result, by the system and method according to the preferred embodiments of the invention, additional information can be reliably and easily assigned to a corresponding OCT image.

Within the meaning of the present invention, the term "assigning" not only relates to assigning additional information to the obtained OCT but also to assigning an obtained OCT image to the additional information. Accordingly, the term "correlating" not only relates to correlating additional information with the obtained OCT image but also to correlating an obtained OCT image with the additional information.

Preferably, the data file contains text information and/or graphical information and/or image information, in particular a document or report, relating to the object. Preferred data formats of text information, like a report, are PDF, DOC or TXT.

It is particularly preferred that the file contains at least one photographic image of the object, in particular of the surface of the object or a part thereof, and/or a graphical representation of the object or a part of the object. Both photographic images and graphical representations of the object provide expressive additional information in view of diagnostic purposes. Alternatively or additionally, the file contains a video image of the object, in particular of the surface of the object or a part thereof. A video image of the object preferably comprises a sequence of photographic images of the object. Therefore, all elucidations given herein in context with images, in particular photographic images, apply to video images accordingly. Preferred video image formats are, e.g., avi or mpeg.

Preferably, the photographic image and/or graphical representation of the object or a part thereof may be a survey image which comprises photographic and/or graphical image information of a region of the object, wherein the region of the object is larger than a region of interest (ROI)

of the object from which the OCT image is acquired. It is further preferred that the photographic image of the object and/or graphical representation of the object is an image of a patient's body area where a region of interest (ROI), from which the OCT image is acquired, is located. These preferred embodiments allow for a particularly reliable assignment of an OCT image to the corresponding location on the object as well as a comfortable retrieval of the OCT image by the survey image or photographic image, respectively.

Alternatively or additionally, the photographic image of the object may be a microscopic image which comprises photographic image information of a region of interest (ROI) of the object from which the OCT image is acquired. This allows for a particularly precise assignment of an OCT image to a specific location on the object.

It may also be of particular advantage if the photographic image of the object is a photographic color image of the object. Alternatively or additionally, the graphical representation of the object may also a color representation of the object. By this, the reliability of assigning positional information to the OCT image is further enhanced and, due to color images or color representation, the additional information is enriched by possibly further diagnostically relevant information, e.g. color or appearance of skin parts from which the OCT image is obtained.

According to another preferred embodiment, the photographic image and/or graphical representation of the object is provided with at least one mark or symbol corresponding to or denoting a position on the object at which an OCT image was or is acquired. Preferably, the photographic image and/or graphical representation of the object together with the at least one mark or symbol is displayed on a display and, upon selection of the at least one displayed mark or symbol by a user, an OCT image acquired at the corresponding position on the object is displayed on the display. These preferred embodiments further contribute to increase the reliability of the assignment of an OCT image to the corresponding location on the object as well as the comfortable retrieval of the OCT image by the photographic image and/or graphical representation of the object.

According to an additional or alternative aspect of the invention, the OCT system examines, in particular continuously, whether a photographic image of the object, in particular of the surface of the object, is available to the OCT system.

The system is preferable configured such that in the case that an OCT image acquisition session of the OCT system is running and a photographic image is available to the OCT system, the control unit of the OCT system indicates to a user that a photographic image is available.

Preferably, it is indicated to a user that a photographic image is available by displaying a pop-up window on the display of the OCT system.

Further, the system is preferable configured such that in the case that an OCT image acquisition session of the OCT system is running and a photographic image is available to the OCT system, the user is requested as to whether the available photographic image shall be stored in the file and/or shall be assigned to or correlated with the OCT images acquired at the current OCT image acquisition session.

Moreover, the system is preferably configured such that in the case that a photographic image of the object is available, in particular available to the OCT system, the photographic image and the OCT image are stored in a memory such that the stored OCT image contains information relating to the photographic image or a storage address of the stored photographic image and/or the stored photographic image contains information relating to the OCT image or a storage address of the stored OCT image.

The above-mentioned additional or alternative aspects of the invention are based on the approach that photographic images of an object, which were acquired by a photographic camera, like a digital camera, a microscopic camera, a USB microscope, a smart phone comprising a camera or a tablet PC comprising a camera, can be provided, e.g. sent, transferred or communicated, to the OCT system by which OCT images of the object, in particular of certain regions of interests (ROI) of the object, are acquired in an OCT image acquisition session. As a camera a dermatoscopic camera or any other digital imaging device used in dermatology can also be used.

Therefore, preferred embodiments of the invention also relate to a photographic camera for acquiring photographic images of an object, in particular a biological tissue like the skin of a human or animal being, which is designed such that an acquired photographic image can be provided, in particular sent or communicated, to the system for optical coherence tomography (OCT).

The term "camera" or "photographic camera" in the context of the invention is not limited to photographic cameras in the narrower sense, i.e. cameras for acquiring, in particular digital, photographs or photographic images, but also comprises other image acquisition systems allowing for an acquisition of electromagnetic radiation images, in particular in the visible spectral range, e.g. microscopes, epi-illumination imaging systems, trans-illumination imaging systems and fluorescence imaging systems.

In the context of the invention, a photographic image is preferably acquired from the skin of a patient. Alternatively or additionally, a photographic image can also be acquired from the whole patient or from a patient's body area where a region of interest, e.g. a skin lesion or similar, is located.

Moreover, the above-mentioned preferred embodiments are not restricted to photographic images as such. Alternatively or additionally, documents and/or reports and/or any kind of files containing text and/or graphical and/or information relating to an object can be provided, e.g. sent, transferred or communicated, to an OCT system by which OCT images of the object, in particular of certain regions of interests (ROI) of the object, are acquired in an OCT image acquisition session.

Accordingly, all elucidations given with respect to photographic images also apply mutatis mutandis to documents and/or reports and/or any kind of files containing text and/or graphical and/or image information relating to the object.

Preferably, the camera is provided with a camera control unit by which acquired photographic images can be selected by a user and subsequently sent to the OCT system via a data communication between the camera and the OCT system. The camera control unit is designed such that it can execute a corresponding application computer program, a so-called "App". The data communication between the camera and the OCT system can be based on a wire-bound connection, like via local area network (LAN), universal serial bus (USB) or the internet, or a wireless connection, like Bluetooth.

The OCT system is preferably provided with a control unit which is designed for examining whether a photographic image is available, e.g. by checking whether a photographic image has been provided or sent by the camera to the OCT system and/or by checking whether a photographic image is present, i.e. stored, in a pre-defined memory, wherein the pre-defined memory is preferably part of the OCT system, in particular part of the control unit.

In the case that the examination yields that a photographic image is available while an OCT image acquisition session is running, i.e. while an OCT image of the object has recently been acquired or is to be acquired soon, the photographic image is displayed on a display unit, preferably a display unit of the OCT system. Alternatively, only an indicator showing the availability of a photographic image is displayed.

Moreover, the control unit can be designed so that it gives a request to a user for an input whether the available photographic image shall be imported and/or stored and/or assigned to and/or correlated with the OCT image which has been or will be recorded in the current OCT imaging acquisition session. Preferably, depending on the user-input the available photographic image will be assigned to and/or correlated with the OCT image which has been or will be recorded in the current OCT imaging acquisition session so that a unique and/or bijective and/or unambiguous allocation of the photographic image and the OCT image is achieved.

The above-mentioned additional or alternative aspects of the invention allow for a convenient and safe acquisition, transfer and addition of supplemental diagnostic information in the form of photographic images and/or graphical representations of an object to OCT images of the object.

In a method for optical coherence tomography according to a more generalized approach an OCT image of an object, in particular a biological tissue like the skin of a human or animal being, is acquired by an OCT system comprising an interferometer and a detector, wherein the object is irradiated with light emitted by the interferometer, light reflected by the object is fed back into the interferometer and detected by the detector and an OCT image of the object is derived from the detected light.

A system for optical coherence tomography for acquiring an OCT image of an object, in particular a biological tissue like the skin of a human or animal being, according to a more generalized approach comprises an interferometer for outputting light with which the object can be irradiated, a detector for detecting light which is reflected by the object and fed back into the interferometer and a control unit for deriving an OCT image of the object from the detected light.

Preferably, the OCT image is encoded in a first image data format and the photographic image and/or the graphical representation of the object is encoded in a second image data format, wherein the second image data format is different to the first image data format.

Preferably, at least one photographic image and/or the graphical representation of the object, which is encoded in the second image data format, is converted and/or incorporated into the first image data format of the OCT image.

Preferably, the first image data format corresponds to the DICOM format. A single DICOM file contains both a header which stores information about, e.g., the patient's name, the type of scan, image dimensions, etc., as well as all of the OCT image data which can contain information in three dimensions. The use of the DICOM format as the first image data format has the additional advantage that standardized reader software for DICOM files exists so that a possibly available proprietary reader software of the OCT system is not mandatory in the case that the OCT image file together with the converted or incorporated file with additional information has to be read by another instance, e.g. by an external physician, where the OCT system is not available.

The term "DICOM format" in the sense of the present invention also comprises the so-called DICOMDIR format, with comprises one or more DICOM format files in a directory or folder, in particular a directory structure or folder structure.

Preferably, the second image data format corresponds to one of the following formats: JPEG, TIFF, PNG, BMP, GIF or PDF.

Preferably, the first image data format, in particular the DICOM format, of the OCT image comprises a header section and an image data section, wherein the header section contains general information related the OCT image, e.g. object ID, type of examination or OCT image dimensions, and the image data section contains image data of the OCT image, image data of the at least one photographic image and/or the graphical representation of the object are incorporated into the header section of the first image data format of the OCT image.

Preferably, the OCT image in the first image data format is stored in a memory, wherein the header of the OCT image in the first image data format contains the image data of the photographic image and/or the graphical representation of the object.

The preferred embodiments elucidated above are based on the approach to assign additional information relating to the object, like a photographic image and/or a graphical representation of the object and/or additional text information, to an OCT image by incorporating data of the data file of the additional information into the data file of the corresponding OCT image. For example, data of a photographic or graphical image data file of a first data format, like JPEG or GIF, are incorporated into the OCT image data file of a second data format, in particular DICOM. In this way, a particularly reliable assignment or correlation of additional information relating to the object, on the one hand, to/with an OCT image, on the other hand, is achieved in a very simple way. As a result, when retrieving an accordingly stored OCT image data file, corresponding additional information, in particular photographic and/or graphical image data, are retrieved at the same time and vice versa.

Preferably, the photographic image of the object is provided to the OCT system by data communication connection between the camera and the OCT system. Preferably, the data communication connection is a wireless data connection. Alternatively, any other kind of communication path is also allowed, e.g. a wire-bound data connection.

Preferably, the camera comprises a camera control unit by which image data of the photographic image are provided, in particular sent or transferred, to the OCT system. Preferably, the image data of the photographic image are provided to the OCT system upon selection of a photographic image from a list of photographic images displayed at the camera. Preferably, the selection of a photographic image from a list of photographic images displayed at the camera is done by a user. Preferably, the image data of the photographic image are provided to the OCT system upon a corresponding command given by a user. Preferably, a command for providing the image data of the photographic image to the OCT system is given by activation of a corresponding button at the camera or icon displayed on the display of the camera. Alternatively or additionally, a user command can also be given by, e.g., language statements of the user, i.e. commands or instructions by the user's voice, or gestures of the user performed in space and/or on the display. Accordingly, a respective command receiving unit, e.g. a speech recognition unit and/or a gesture recognition unit and/or a touch screen, is provided. Preferably, the assigned photographic image and OCT image of the object are displayed simultaneously on a common display.

Further advantages, features and examples of the present invention will be apparent from the following description of following figures:

DETAILED DESCRIPTION OF THE PREFERRED EMBODIMENTS

Figure 1:
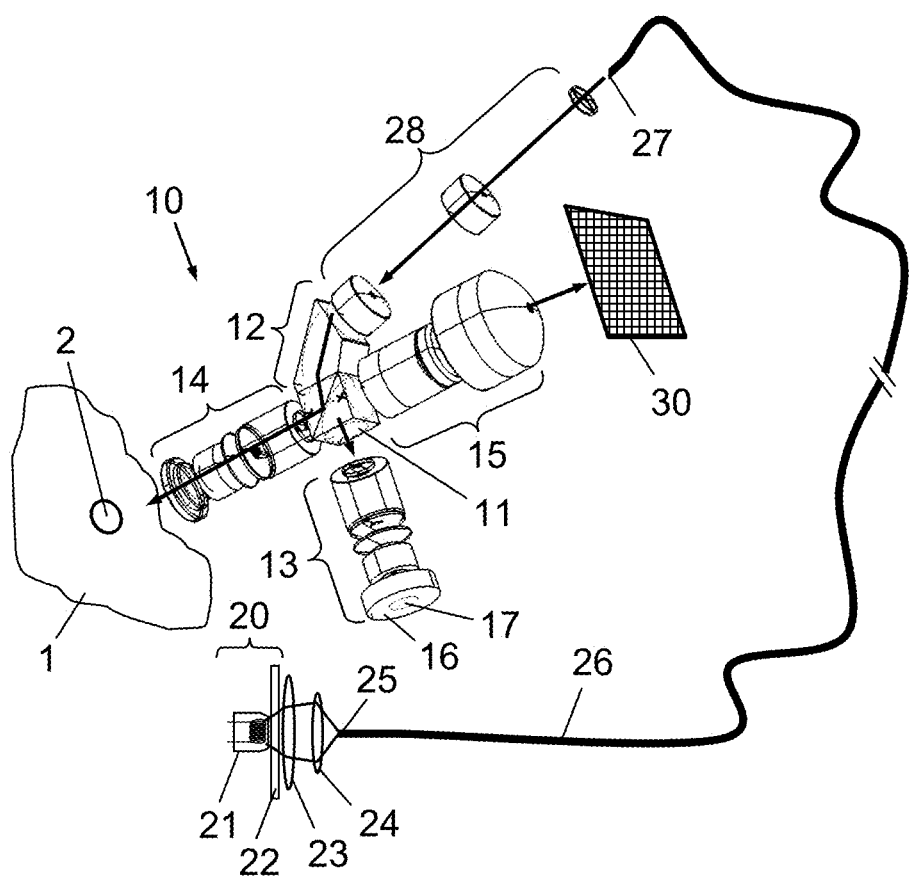
FIG. 1 shows an example of a part of an OCT system.

FIG. 1 shows a schematic representation of an example of a part of an OCT system comprising an interferometer 10 with a beam splitter 11, an illumination arm 12, a reference arm 13, a sample arm 14 and a detector arm 15. Moreover, an illumination light source 21 is provided for generating light which is filtered by an optical filter 22 and focused into the entrance region 25 of a light guide 26 by optics which comprises lenses 23 and 24.

The light coupled into the light guide 26 is coupled into the illumination arm 12 of the interferometer 10 by optics 28 located at the exit region 27 of the light guide 26. The light reaches the beam splitter 11 by which the light is forwarded to the reference arm 13 and reflected on a reference mirror 16 located at the end of the reference arm 13. On the other hand, a part of the light passes the sample arm 14 and illuminates an area 2 of an object 1. The object is preferably a biological tissue, in particular the skin of a human being.

The light reflected, in particular back-scattered, by the object 1 passes again the sample arm 14 and is superimposed in the beam splitter 11 with light reflected by the reference mirror 16 of the reference arm 13. The superimposed light finally reaches by passing the detector arm 15 the detector 30 which comprises a plurality of detector elements which are arranged along a, preferably plane, area and therefore enables a spatially resolved acquisition of the light reflected or scattered by the object 1, in particular the detection of a corresponding interference pattern.

Preferably, the detector 30 comprises a CMOS camera, the detector elements of which are sensitive in the infrared spectral range, in particular in a spectral range between approximately 1250 nm and 1350 nm. Preferably, the CMOS camera has 512×640 detector elements.

Figure 2:
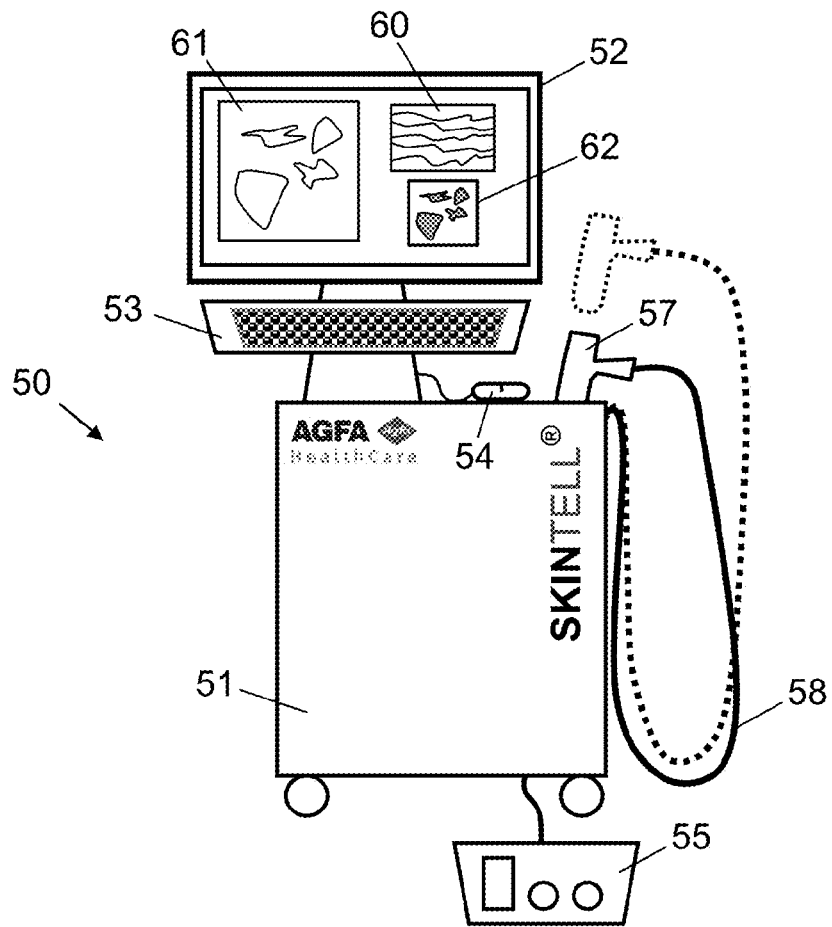
FIG. 2 shows an example of an OCT system.
Figure 2:
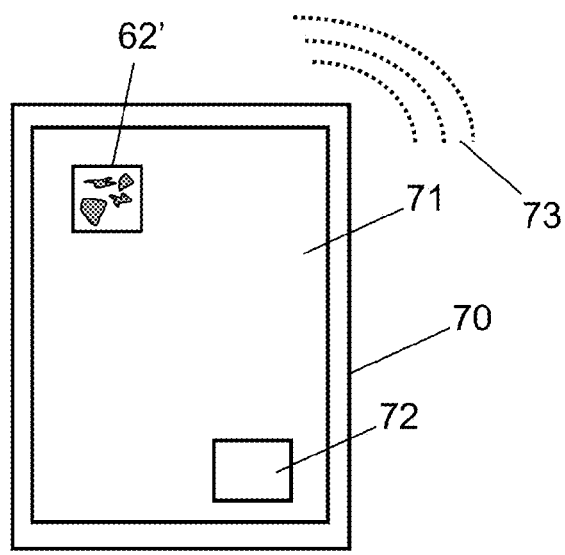

FIG. 2 shows an example of an OCT system 50 comprising a housing 51, input elements in form of a keyboard 53, a computer mouse 54 as well as a pedal control unit 55. The OCT system 50 is also called "SKINTELL" which is a registered trade mark of Agfa HealthCare N.V., Belgium.

The system 50 further comprises a sensor head 57 which is connected with the housing 51 via a cable 58 or a cable conduit. In its rest position, the sensor head 57 is plugged into a holder provided at the housing 51 and can be removed from the holder—as indicated by dotted lines of the sensor head 57 and the cable 58—when OCT images shall be acquired.

The system further comprises a display 52 in form of a flat screen on which OCT images 60 and 61, which were acquired from the object 1, in particular a patient, by setting the sensor head 57 onto the object 1, in particular onto a patient's skin.

On the display 52 of the OCT system 50 a photographic image 62 of the object 1 is displayed in addition to the OCT images 60 and 61. The photographic image 62 has been acquired by a photographic digital camera 70 which can be, for example, a usual digital camera, a smart phone, a tablet PC or a digital microscope. The camera 70 comprises a camera display 71 which displays one or more photographic images 62' acquired by a photographic image acquisition unit (not shown) of the camera 70, preferably comprising one or more optical lenses and a CCD array for converting light received from the object 1 into spatially resolved photographic image data of the object 1. Upon activation of a respective selection button 72 by a user, the photographic image data of the captured photographic image 62' are sent by a wireless communication connection 73 to the OCT system 50 and received by the latter.

A control unit (not shown) of the OCT system 50 continuously examines whether photographic image data are available or have been sent to the OCT system 50 and, in the affirmative case, gives the user a notice that a photographic image is available, for example by a pop-up window at the display 52 of the OCT system 50 showing the transmitted photographic image and requesting the user for an input whether the available photographic image shall be imported and/or assigned and/or correlated with the one or more OCT images 60 and 61 which have been or will be acquired from the same object 1. In the case that the user decides to accept the available photographic image 62, the latter will be stored in a memory of the OCT system 50 and/or displayed on the display 52 of the OCT system 50.

The method and system 50 described above allows for a very convenient and safe acquisition, transfer and addition of photographic image information of an object to OCT images acquired from the same object. This considerably helps the user, in particular a medical practitioner, to identify the location on the object 1 on which or from which OCT images 60 and 61 were acquired.

In particular, the system 50 and/or the camera 70 is/are designed for executing a method, in particular in form of a software package, for wireless transfer of, in particular jpeg, images from a smart phone operating system, in particular iOS, to a windows PC (XP SP3; 7). The image transfer is easy and fast for the user. Preferably, a graphical user interface (GUI) on the iOS guides the user intuitively (no reading of user manual up-front necessary).

Preferably, the OCT system 50 and/or a component thereof is designed for importing JPG images stored on a storage medium that is available in the OS of a camera 70 into the OCT system 50. It is possible to import a JPG image to the OCT system via bluetooth or WiFi from a registered device, like a smart phone. Preferably, the method or system comprise the following steps and/or features, wherein unless otherwise stated, the term "image" or "images" refers to photographic image(s):

A button "Import image from file" located at the lower edge of the screen 52 (in row with export buttons) shall trigger the import from file.

Bluetooth or WiFi import: a window will pop up automatically as soon as a file was sent to the PC of the OCT system 50 via bluetooth or WiFi hardware.

The application running at the control unit of the OCT system 50 supervises a folder (configurable in the *.ini); if a jpg or jpeg image is added to this folder, a window pops up automatically. Preferably, any other file-extension shall be ignored.

Import of images (bluetooth, WiFi and from file) is possible if a session is open or in a scanning mode, i.e. a mode in which an OCT image has been or is to be acquired.

It is possible to add images to an old, i.e. previous, session which was opened via an "admin screen".

Clicking on "Import image from file" opens a context menu that allows to chose an image file from all available storage media (hard disk; USB stick; camera . . . ) pre-select only "*.JPG and *.JPEG".

The image will be displayed in the main view window and in a thumbnail list after import.

Default size of the image frame is maximum 1200 pixels wide and/or maximum 1000 pixels high, dependent on image ratio which limit should be applied.

Default display of image fits the image into an image frame but shall not distort the image (after choosing image from thumbnail list); (e.g. an image with 2000×500 pixels is displayed as 1200×300; or an image with 1200×1800 pixels is displayed as 667×1000).

Preferably, the system is configured such that an image distortion shall not be possible.

The image size is scaled at import to 4000 pixels if image width or height is larger than 4000.

It is possible to add an image comment to imported images.

Imported images appear in HTLM reports in the same manner as SKINTELL images, i.e. OCT images.

Export as TIFF is not mandatory for imported images but is allowed.

Imported images are stored in the data base in the same way as SKINTELL images, i.e. OCT images.

A session contains both SKINTELL images, i.e. OCT images, and imported images, i.e. photographic images.

Re-calling a session can show all SKINTELL images, i.e. OCT images, and imported images.

A DICOM export includes imported images.

A folder clean-up is performed at start-up of SKINTELL only, wherein files older than two days are deleted.

If an image is added via BlueTooth or WiFi and the OCT system 50 is in compare screen mode, the jpg or jpeg are always added to the left session.

If the OCT system 50 is in compare screen mode and the same session is open on both sides, the jpg/jpeg images are added to this session and are displayed in both thumbnail lists.

In the following, the assigning of additional information in form of photographic images and/or a graphic representation of an object, in particular a patient, to OCT images obtained from the object will be elucidated in more detail.

Figure 3:
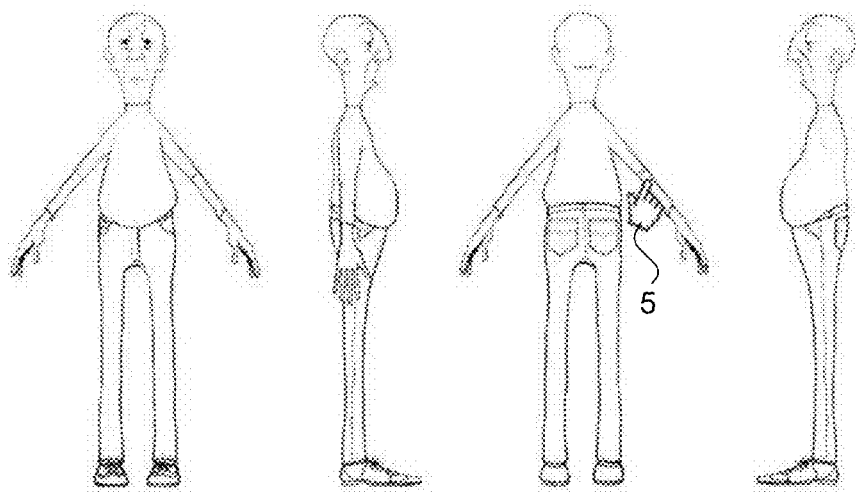
FIG. 3 shows examples of a graphic representation of a whole patient (upper part of figure) and of a patient's part (lower part of figure)
Figure 3:
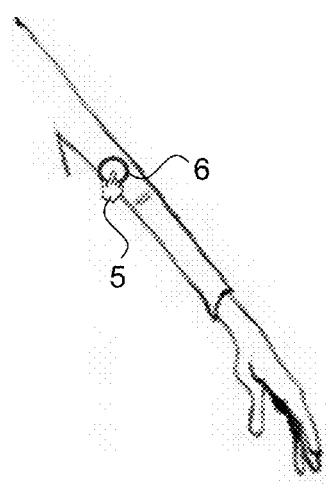

FIG. 3 shows an example of a graphic representation of a whole patient (upper part) and of a patient's region (lower part) in form of line drawings. Such a mere graphical representation is preferred in the case that no photographic images are available or were imported. The graphical representations are displayed preferably on the display 52 of the OCT system 50 (see FIG. 2) when the latter is in a diagnostic mode in which OCT images 60, 61 are acquired. Preferably, the graphical representations of the patient are displayed on the display 52 instead of or in addition to a photographic image 62 of the patient or a part of the patient.

By the displayed graphic representation of the patient or a patient's part, a user can pre-define regions of interest and/or suspicious regions on the body of a patient under examination by selecting a body region, like the arm (upper part of FIG. 3), and/or by selecting an exact location or position on a displayed part of the object, for example on the arm (lower part of FIG. 3), e.g. by a mouse pointer 5. Preferably, the selected location on the graphical representation of the body part, e.g. the arm, is labeled with a mark 6, like a circle, which is visible to the user.

Figure 4:
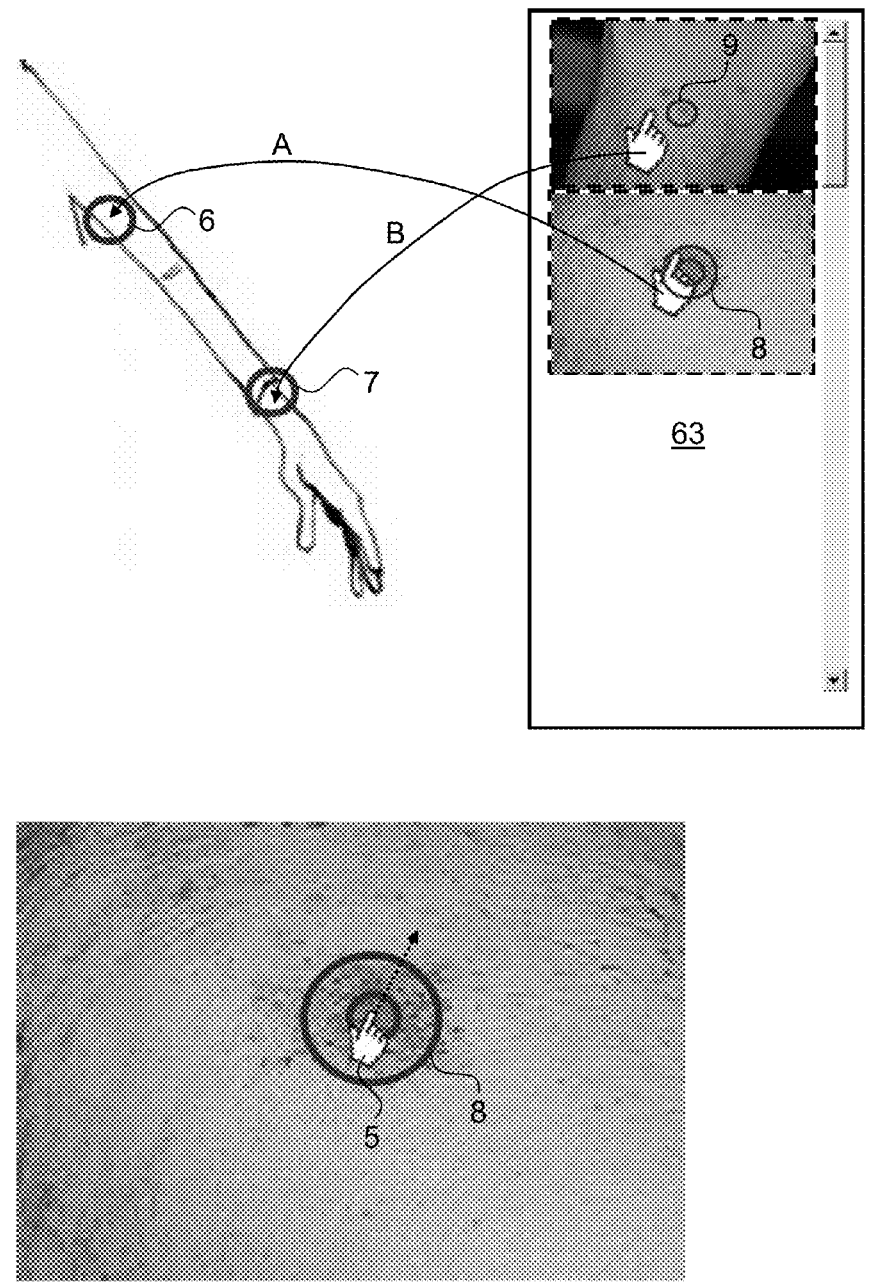
FIG. 4 shows an example of a graphic representation of a patient's part together with examples of imported photographic images obtained from areas of the patient's part.

Upper part of FIG. 4 shows an example of a graphic representation of a patient's arm which is displayed, preferably on display 52 of OCT system 50 (see FIG. 2), together with a list 63 of imported photographic images obtained from different areas of the patient's arm.

After an initial selection of a body region, i.e. the arm, by the user (see upper part of FIG. 3), the system is configured such that the user can define exact locations on the displayed body region, e.g. on the upper arm or near the wrist, preferably by dragging (see arrows A and B) a photographic image from the displayed list 63 of photographic images to the corresponding position on the displayed representation of the arm. In the graphical representation of the arm, respective positions are automatically labeled with marks 6 and 7, respectively. By this, photographic images 63 of areas of a patient or a patient's part can be exactly and intuitively assigned to corresponding locations on the displayed body region.

Preferably, the photographic images 63 may also contain marks 8, 9 indicating one or more positions or regions of interest, in particular positions or regions of the body from which OCT images were or have to be obtained. Preferably, the size of the marks 6 to 9 displayed in the graphic representation and/or the photographic images 63 can be changed by zooming a mark, e.g. mark 8, from its center, e.g. by a mouse pointer 5 as illustrated by dashed arrow in the lower part of FIG. 4.

Figure 5:
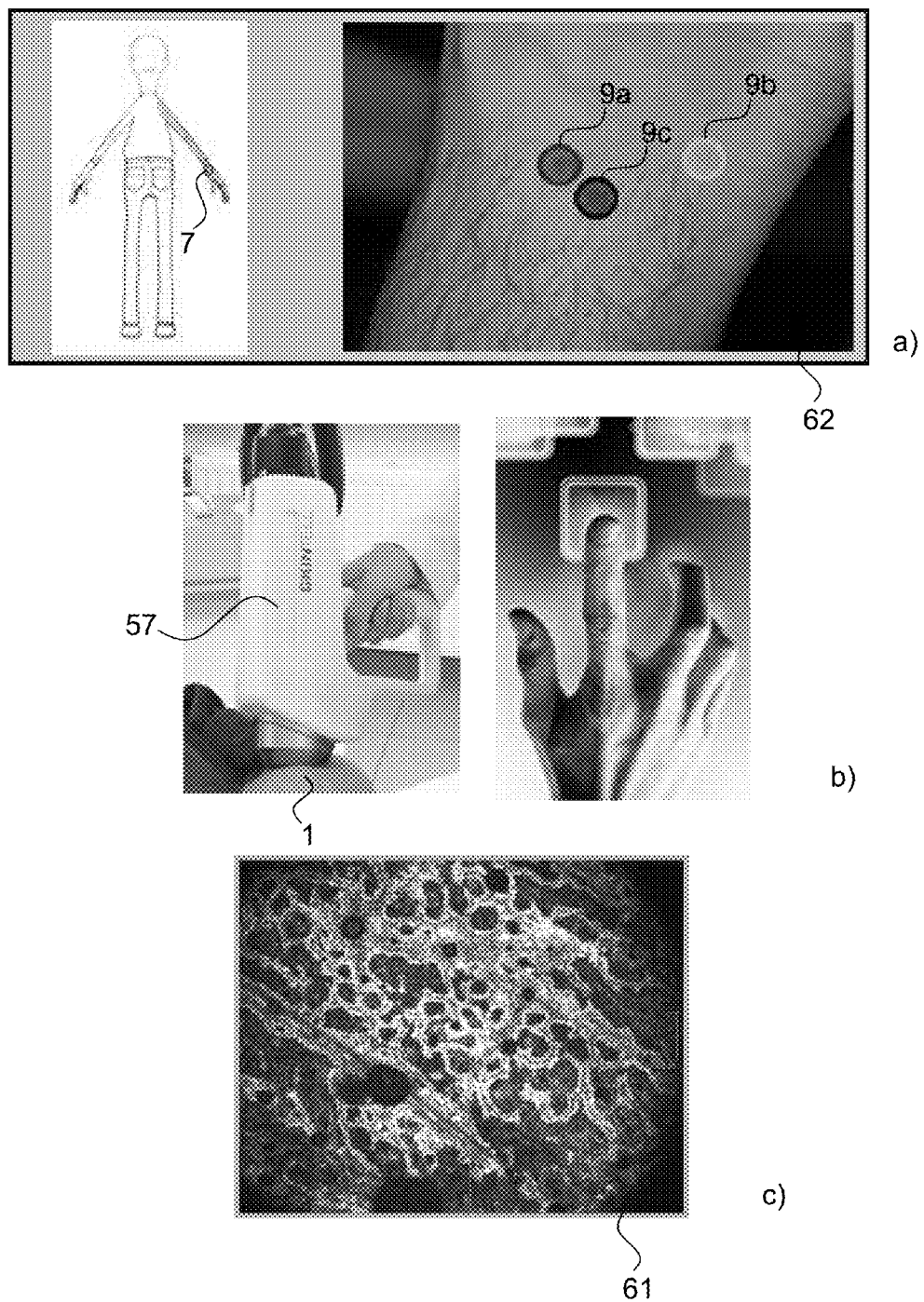
FIG. 5. shows an example of a preferred workflow for assigning graphical information and/or photographic images to OCT images.

FIG. 5 shows an example of a preferred workflow for assigning graphical information and/or photographic images to OCT images.

In a first step, as illustrated in FIG. 5a), at least one photographic image 62 of an area on the patient's skin is imported into the OCT system 50 and provided with marks 9a to 9c indicating regions of diagnostic interest on the area and, preferably, assigned to the corresponding location, see mark 7, on a graphical representation (left part of FIG. 5a) of the respective body region as elucidated in detail above, preferably by dragging and dropping the image 62 to the according location on the graphical representation of the patient. In the case that no photographic image has been imported, only the graphical representation is provided with an according mark 7.

In a second step, as illustrated in FIG. 5b), the sensor head 57 (see FIG. 2), in particular a light outlet and inlet window of the sensor head 57, is placed onto an area of the skin of the patient 1 corresponding to the area from which the displayed photographic image 62 was obtained and/or corresponding to the location of mark 7 on the graphical representation of the patient. In particular, the sensor head 57 is placed onto a region of interest on the patient's skin corresponding to the location which is indicated by one of the marks 9a to 9c on the photographic image 62.

Preferably, the system is designed such that a user can toggle between marks 7 and/or 9a to 9c. This can be achieved, e.g., by pressing a button, like a button at the sensor head 57, keyboard 53, mouse 54 and/or pedal control unit 55, or by any other control element. In general, the system may be configured such that toggling is not only possible between marks 7 and 9a to 9c of the same body part but also between marks on different body parts. By this, one of the marks 7 and 9a to 9c can be easily selected by the user before the sensor head 57 is placed onto the location on the patient's skin corresponding to the position of the selected mark 7 and 9a to 9c.

In a third step, as illustrated in FIG. 5c), acquisition of an OCT image 61 from the region of interest, onto which the sensor head 57 is placed, is initiated, preferably by pressing the same or another button, in particular a button at the sensor head 57, keyboard 53, mouse 54 and/or pedal control unit 55, or by any other control element. Subsequently, the acquired OCT image 61 is stored and assigned to the graphical representation of the patient and/or to the photographic image 62 of the corresponding area, preferably together with respective marks 7 or 9a to 9c.

The workflow elucidated above is of particular advantage if body locations of interest have already been defined before corresponding OCT images are acquired.

Figure 6:
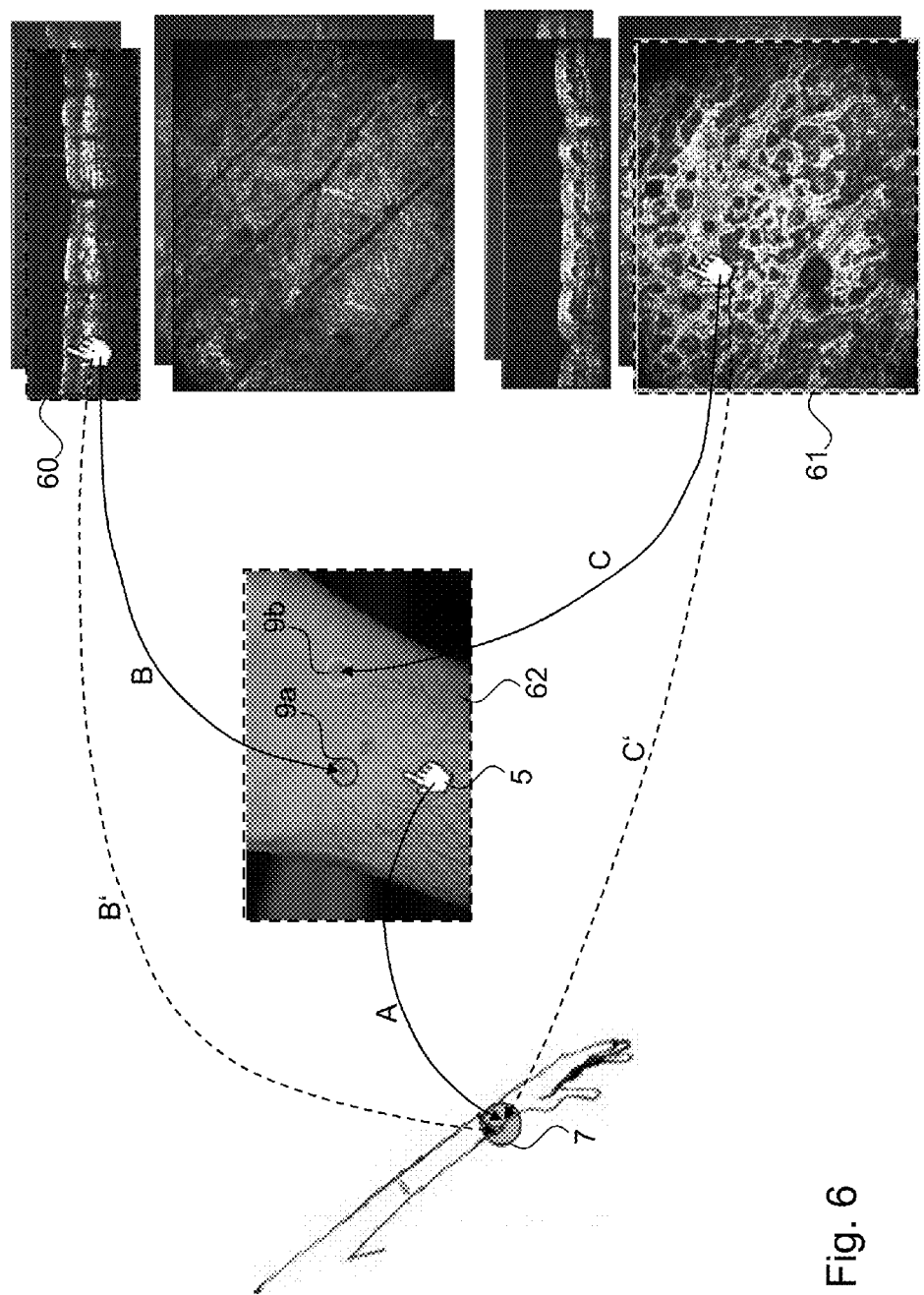
FIG. 6 shows another example of a preferred workflow for assigning graphical information and/or photographic images to OCT images.

FIG. 6 shows another example of a preferred workflow for assigning graphical information and/or photographic images to OCT images. This workflow allows for an assignment of OCT images to corresponding body locations after the OCT images have been obtained.

In a first step, an imported photographic image 62 of an area of the patient's skin is assigned to the corresponding location on a graphical representation of the patient by dragging (see arrow A) and dropping the photographic image 62, e.g. by a mouse pointer 5, to the corresponding location on the graphical representation, whereupon the location is labeled with a corresponding mark 7.

In a second step, a previously acquired OCT image 60 is dragged (see arrow B) and dropped, preferably by a mouse pointer, to a location 9a on the displayed photographic image 62, which corresponds to the location of the region of interest on the patient's skin from which the selected OCT image 60 was obtained. Same applies accordingly to a further OCT image 61, which is dragged (see arrow C) and dropped to location 9b on the displayed photographic image 62.

Preferably, the system is configured such that in the case that no photographic image 62 is available, an OCT image 60, 61 can be dragged (see dashed arrows B' and C') and dropped to a location (see mark 7) on the displayed graphical representation of the patient's part, wherein the location corresponds to the region of interest from which the selected OCT image 60, 61 was obtained.

The workflows elucidated above allow for a particularly reliable retrieval of OCT images, in particular when a follow-up diagnosis is carried out. This will be elucidated in detail in the following.

Figure 7:
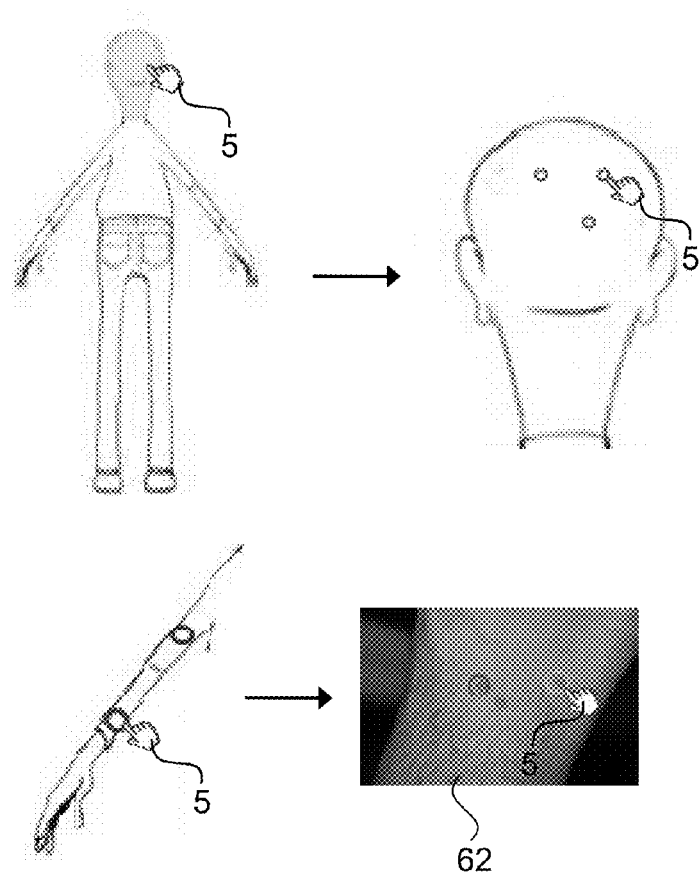
FIG. 7 shows graphical representations and a photographic image for the illustration of workflows for retrieving OCT images.

FIG. 7 shows graphical representations and a photographic image of the patient or a patient's part, respectively, by which workflows for retrieving OCT images are illustrated.

As shown in the upper part of FIG. 7, from a graphical representation of the whole body of the patient a part, e.g. the head, can be selected, preferably by a mouse pointer 5. In the case that OCT images were previously assigned to a graphical representation of this part, an enlarged representation of the selected part appears, in which the exact locations of the corresponding regions of interest on the patient's skin, from which OCT images were obtained, are labeled with corresponding marks. By selecting the marks, e.g. by a mouse pointer 5, the corresponding OCT image can be retrieved and displayed.

Alternatively or additionally, as illustrated in the lower part of FIG. 7, from a graphical representation of a part of the body of the patient a region, e.g. near the wrist, can be selected, preferably by a mouse pointer 5. In the case that at least one photographic image 62 was previously assigned to this region, the at least one photographic image 62 appears upon selection of this region in the graphical representation. Further, in the case that OCT images were assigned to the photographic image 62 of this region, the exact locations of the regions of interest on the patient's skin, from which the OCT images were obtained, are labeled with corresponding marks in the displayed photographic image 62. By selecting these marks, e.g. by a mouse pointer 5, the corresponding OCT images can be retrieved and displayed.

Figure 8:
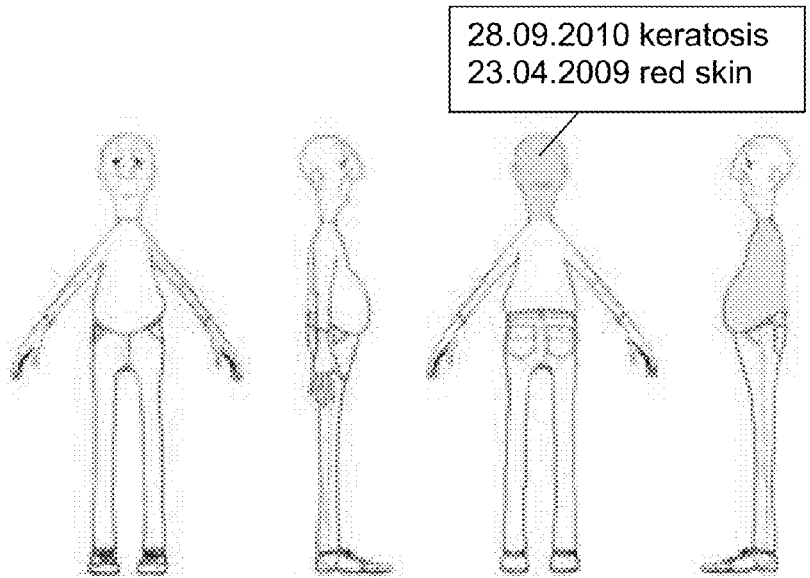
FIG. 8 shows graphical representations for the illustration of a further workflow for retrieving OCT images.
Figure 9:
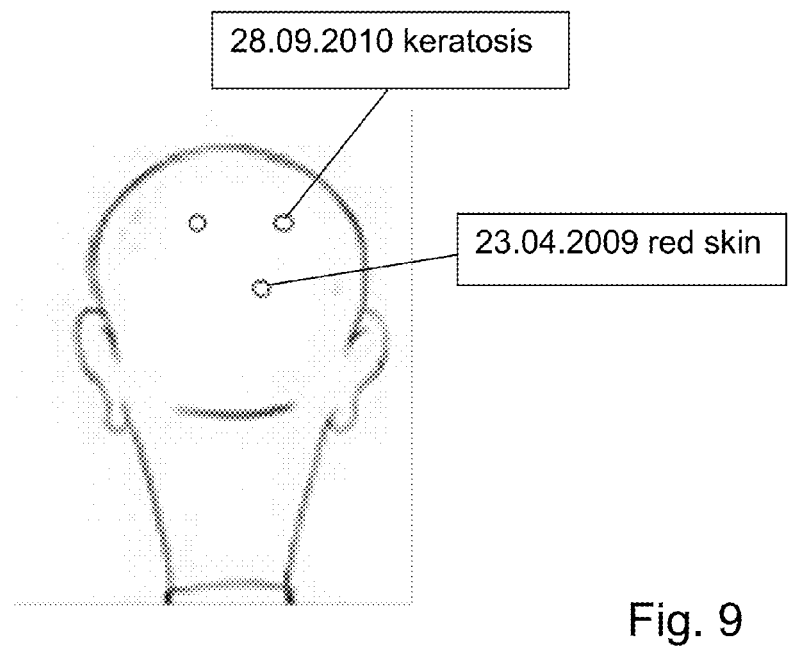
FIG. 9 shows another graphical representation for the illustration of a further workflow for retrieving OCT images.

FIGS. 8 and 9 show graphical representations for the illustration of further examples of workflows for retrieving OCT images, which are of particular advantage in the case that a large number of consultations were made and/or a large number of regions of interest of the patient were investigated. A large number in this context is a number which preferably exceeds 12 or 16.

In order to avoid a confusion of the user due to large numbers of corresponding marks on the respective representation of the body or body part, the system is configured such that in an initial step a body region in the graphical representation of the body is highlighted when a pointing element, e.g. a mouse pointer 5, is over the body region, as shown in the posterior view of the graphical representation of the patient in FIG. 8, where the mouse pointer 5 is located over the head. Preferably, this body region is highlighted in the presence of the pointing element 5 only in the case that additional text information and/or OCT images were assigned to this body region. Additionally or alternatively to a highlighting of the body region, an information on possibly available prior consultations and/or OCT image recordings is displayed, e.g. date and clinical findings and/or symptoms, as exemplarily shown in FIG. 8.

After the body part has been selected, an enlarged representation of this body part is displayed (see FIG. 9) which is labeled with marks at the exact locations of regions of interest from which OCT images were acquired. Additionally, the system is configured such that when the mouse pointer is over a mark, an information on possibly available prior consultations and/or OCT image acquisitions is displayed, e.g. date and clinical findings and/or symptoms.

Figure 10:
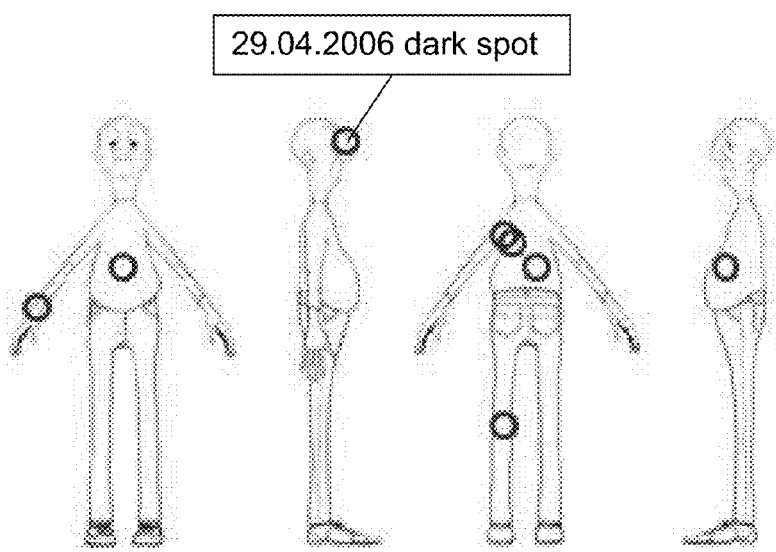
FIG. 10 shows graphical representations for the illustration of yet another workflow for retrieving OCT images.

FIG. 10 shows graphical representations of the patient's body for the illustration of a further example of a workflow for retrieving OCT images, which is of particular advantage in the case that only a small number of consultations were made and/or a small number of regions of interest of the patient were investigated. A small number in this context is a number which is preferably smaller than 12 or 16.

In this case, an initial pre-selection of a relevant part of the body, as elucidated above in connection with FIG. 8, may be omitted. Rather, according marks are displayed directly on the graphical representations of the whole body, as illustrated in FIG. 9. As for the rest, the elucidations in connection with FIG. 9 apply accordingly.

The examples of workflows and functionalities elucidated above allow for a comfortable and reliable retrieval of OCT images by correspondingly marked graphical representations and/or photographic images of the patient's body, which are also called "body maps".

Figure 11:
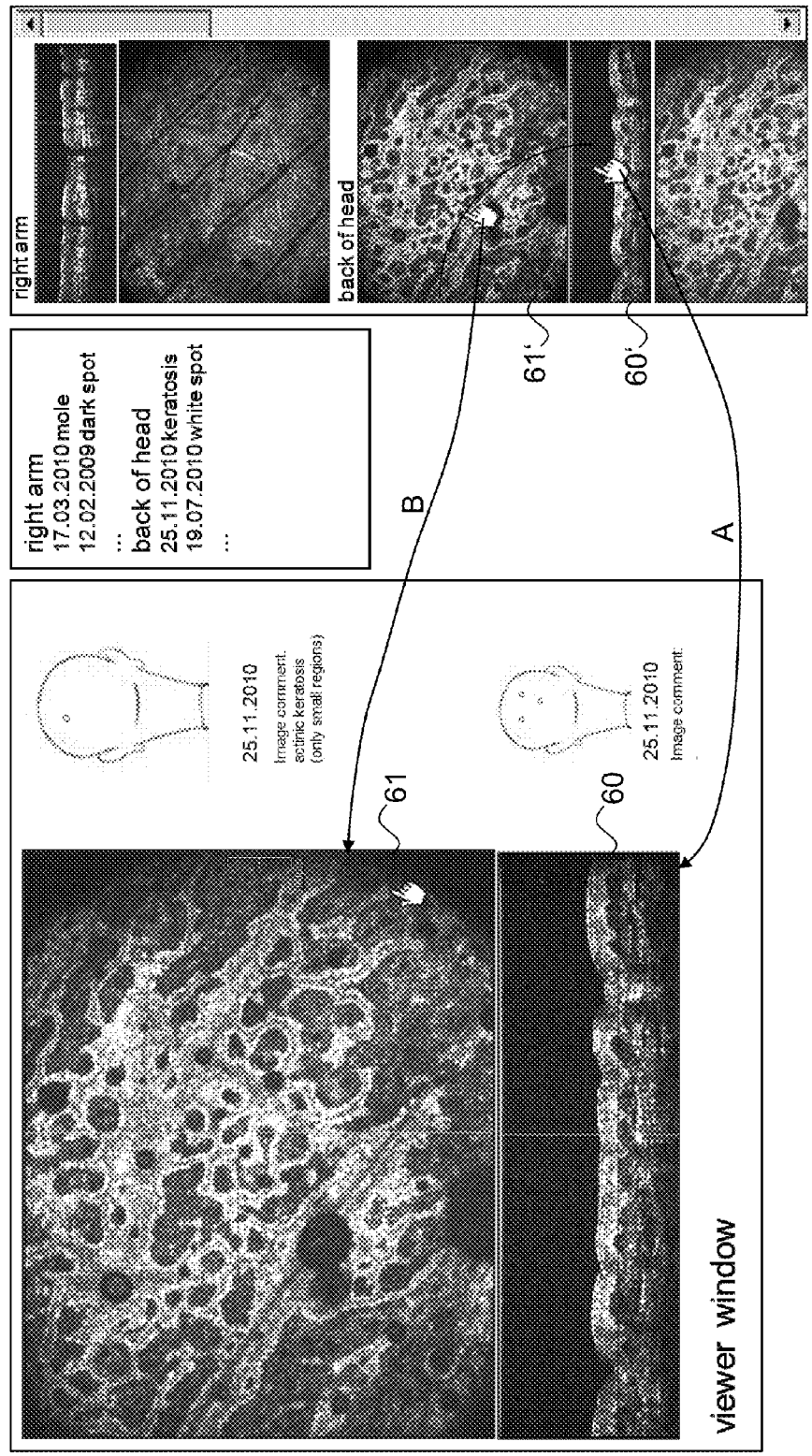
FIG. 11 shows an example of displaying OCT images together with graphical representations of corresponding body parts.

FIG. 11 shows an example of a window on the display 52 of the OCT system 50 (see FIG. 2), where OCT images 60, 61 are displayed together with graphical representations of corresponding body parts including corresponding marks and further textual information, e.g. date of consultation and clinical findings and/or symptoms. Preferably, the system is configured such that the OCT images 60, 61 can be dragged (see arrows A and B) from a displayed list of downscaled OCT images 60', 61' to a viewer window section, where enlarged image 60, 61 are displayed.

As already elucidated above, it is preferred to assign additional information relating to the object, like photographic images and/or a graphical representation of the object and/or additional text information, to an OCT image by incorporating data of the data file of the additional information into the data file of the corresponding OCT image. For example, data of a photographic or graphical image data file of a first data format, like JPEG, TIFF or GIF, are incorporated into the OCT image data file of a second data format, in particular DICOM. This will be elucidated in more detail in the following.

Digital Imaging and Communications in Medicine (DICOM) is a standard for handling, storing, printing and transmitting information in medical imaging. It includes a file format definition and a network communications protocol. The communication protocol is an application protocol that uses TCP/IP to communicate between systems.

In DICOM format, information is grouped into data sets, which means that a file of an OCT image actually contains, i.a., the patient ID within the file, so that the OCT image cannot be separated from this information by mistake. A DICOM data file consists of a number of attributes, including items such as patient name, ID, etc., and one special attribute containing the OCT image pixel data (a single DICOM object can have only one special attribute containing pixel data). Within the meaning of the present invention, a DICOM data file comprises a "header" in form of a list of attributes, like patient ID, as well as only one special attribute in form of pixel data of a single OCT image.

Figure 12:
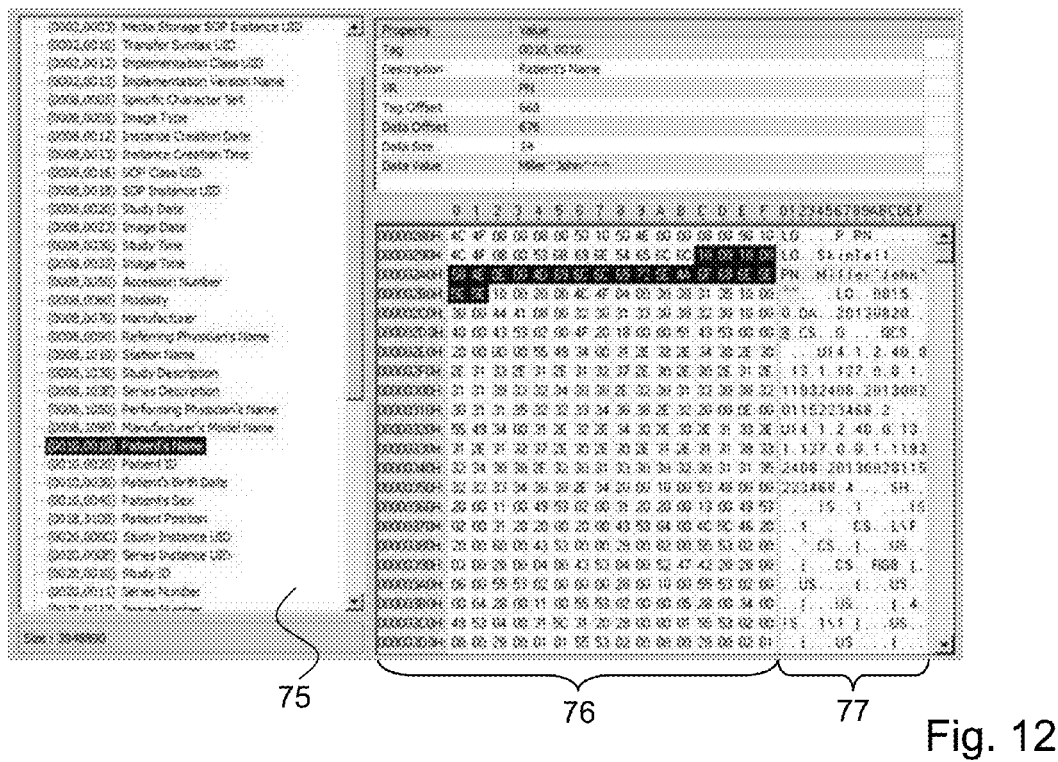
FIG. 12 shows a first schematic representation of the contents of an OCT image data file in DICOM format.

FIG. 12 shows a first schematic representation of the contents of an OCT image data file in DICOM format. The present representation has been established by a DICOM viewer tool which shows a list of attributes 75, i.e. a header, from which "patient's name" was selected. In field 76 storage addresses (left column) and their content (hexadecimal) are displayed, wherein the highlighted sequence contains the patient's name in hexadecimal, which is also displayed in cleartext in field 77 (also highlighted).

Figure 13:
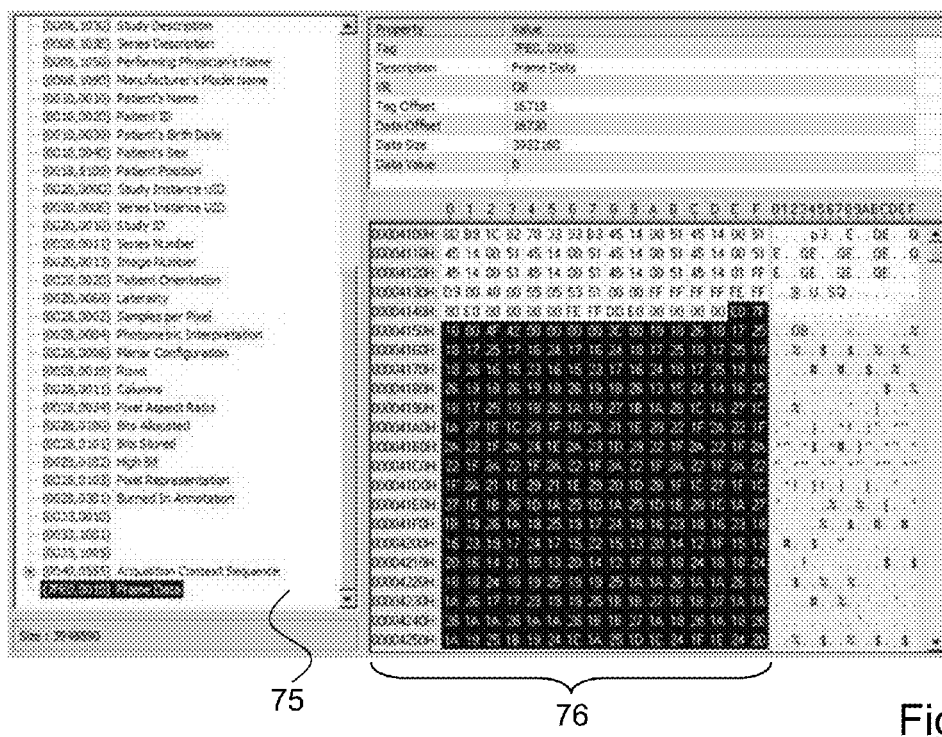
FIG. 13 shows a second schematic representation of the contents of an OCT image data file in DICOM format.

After scrolling down the list of attributes 75 and selecting "frame data", as shown in FIG. 13, in field 76 storage addresses (left column) and content (highlighted) of additional photographic and/or graphical image data relating to the present patient and/or the OCT image obtained from the patient are displayed. As apparent from FIG. 13, additional photographic and/or graphical image data (highlighted) are incorporated in the "header" (list of attributes) of the DICOM file, which also contains OCT image pixel data (not shown) as a special attribute.

By the above-mentioned incorporation of photographic and/or graphical image data into the header of the OCT image data file, which is preferably in DICOM format, a particularly reliable assignment or correlation of additional information relating to the object, on the one hand, to/with an OCT image, on the other hand, is achieved, so that, when retrieving an accordingly stored OCT image data file, corresponding additional information, in particular photographic and/or graphical image data, is retrieved at the same time and vice versa. Accordingly, the OCT image cannot be separated from this additional information by mistake.

The invention claimed is:

1. A method for acquiring an image of an object using an optical coherence tomography system, the method comprising the steps of:
coupling light generated by an illumination light source into an interferometer;
irradiating the object with light emitted by the interferometer and feeding back light reflected by the object into the interferometer;
detecting the light fed back into the interferometer;
deriving an image of the object from the detected light;
examining whether information relating to the object or a portion of the object is available to the optical coherence tomography system, and
when an optical coherence tomography image acquisition session of the optical coherence tomography system is running and the information is available to the optical coherence tomography system:
indicating to a user that the information is available; and
requesting the user for an input whether the information shall be stored in a file and assigned to or correlated with the image of the object; and
depending on the input from the user, assigning or correlating the image of the object to or with, respectively, the file containing the information relating to the object.

2. The method according to claim 1, wherein the file includes graphical information and/or image information relating to the object.

3. The method according to claim 1, wherein the file includes at least one photographic image of the object, at least one video image of the object, and/or at least one graphical representation of the object.

4. The method according to claim 3, wherein the at least one photographic image of the object and/or the at least one graphical representation of the object is a survey image which includes photographic image information and/or graphical information of a region of the object, and the region of the object is larger than a region of interest of the object from which the image is acquired.

5. The method according to claim 3, wherein the at least one photographic image of the object and/or the at least one graphical representation of the object is an image of a patient's body area where a region of interest, from which the image is acquired, is located.

6. The method according to claim 3, wherein the at least one photographic image of the object is a microscopic image which includes photographic image information of a region of interest of the object from which the image is acquired.

7. The method according to claim 3, wherein the at least one photographic image of the object is a photographic color image of the object.

8. The method according to claim 3, wherein the at least one photographic image of the object and/or the at least one graphical representation of the object includes at least one mark corresponding to a position on the object at which the image was acquired.

9. The method according to claim 8, further comprising the step of:
displaying the at least one photographic image of the object and/or the at least one graphical representation of the object together with the at least one mark on a display;
selecting the at least one mark on the display; and
displaying an image acquired at the corresponding position on the object on the display.

10. The method according to claim 1, wherein the image is encoded in a first image data format and the file containing information relating to the object is encoded in a second image data format, which is different from the first image data format, the method further comprising the step of:
converting and/or incorporating the second image data format into the first image data format of the image.

11. The method according to claim 10, wherein the first image data format of the image includes a header section and an image data section, the header section includes general information related to the image and the image data section contains image data of the image, the method further comprising the step of:
incorporating image data of at least one photographic image and/or at least one graphical representation of the object into the header section of the first image data format of the image.

12. The method according to claim 10, wherein the first image data format is a DICOM format.

13. The method according to claim 10, wherein the second image data format is a JPEG, TIFF, PNG, BMP, or GIF format.

14. The method according to claim 1, further comprising the step of:
indicating to a user that a photographic image is available by displaying a pop-up window on a display.

15. The method according to claim 1, further comprising the steps of:
when a photographic image of the object is available, storing the photographic image and the image in a memory such that the stored image contains information relating to the photographic image or a storage address of the stored photographic image, and/or the stored photographic image contains information relating to the image or a storage address of the stored image.

16. The method according to claim 1, wherein the information relating to the object is a photographic image of a surface of the object.

17. A system for acquiring an image of an object using optical coherence tomography, the system comprising:
an illumination light source configured to generate light;
an interferometer into which the light generated by the illumination light source is coupled, the interferometer being configured to output light with which the object is irradiated;
a detector configured to detect light reflected by the object and to feed back the detected light into the interferometer; and
a controller configured or programmed to:
derive an image of the object from the detected light of the object;
examine whether information relating to the object or a portion of the object is available to the optical coherence tomography system, and
when an optical coherence tomography image acquisition session of the optical coherence tomography system is running and the information is available to the optical coherence tomography system:
indicate to a user that the information is available; and
request the user for an input whether the information shall be stored in a file and assigned to or correlated with the image of the object; and
depending on the input from the user, assign or correlate the file containing the information relating to the object to or with, respectively, the image of the object derived by the controller.

18. The system according to claim 17, wherein the information relating to the object is a photographic image of a surface of the object.

* * * * *